(12) United States Patent
Lai

(10) Patent No.: US 9,241,672 B2
(45) Date of Patent: Jan. 26, 2016

(54) DETERMINING USABILITY OF AN ACOUSTIC SIGNAL FOR PHYSIOLOGICAL MONITORING USING FREQUENCY ANALYSIS

(75) Inventor: Yungkai Kyle Lai, Aliso Viejo, CA (US)

(73) Assignee: Sharp Laboratories of America, Inc., Camas, WA (US)

(*) Notice: Subject to any disclaimer, the term of this patent is extended or adjusted under 35 U.S.C. 154(b) by 896 days.

(21) Appl. No.: 13/369,463

(22) Filed: Feb. 9, 2012

(65) Prior Publication Data

US 2013/0211274 A1 Aug. 15, 2013

(51) Int. Cl.
*A61B 5/00* (2006.01)
*A61B 7/00* (2006.01)

(52) U.S. Cl.
CPC .............. *A61B 5/7221* (2013.01); *A61B 5/7225* (2013.01); *A61B 7/00* (2013.01)

(58) Field of Classification Search
CPC .................................. A61B 7/04; A61B 7/003
USPC .......................................... 600/529, 586, 528
See application file for complete search history.

(56) References Cited

U.S. PATENT DOCUMENTS

| | | | |
|---|---|---|---|
| 5,337,251 A * | 8/1994 | Pastor | 702/70 |
| 6,847,933 B1 * | 1/2005 | Hastings | 705/2 |
| 6,947,565 B2 | 9/2005 | Halleck et al. | |
| 7,267,652 B2 | 9/2007 | Coyle et al. | |
| 7,862,515 B2 | 1/2011 | de Chazal et al. | |
| 2003/0018276 A1 * | 1/2003 | Mansy et al. | 600/529 |
| 2005/0187446 A1 * | 8/2005 | Nordstrom et al. | 600/323 |
| 2007/0118054 A1 | 5/2007 | Pinhas et al. | |
| 2007/0239220 A1 * | 10/2007 | Greenhut et al. | 607/32 |
| 2008/0039733 A1 * | 2/2008 | Unver et al. | 600/528 |
| 2008/0306367 A1 | 12/2008 | Koehler et al. | |
| 2009/0149748 A1 * | 6/2009 | Lenhardt et al. | 600/437 |
| 2012/0238834 A1 * | 9/2012 | Hornick | 600/301 |
| 2013/0060150 A1 * | 3/2013 | Song et al. | 600/484 |
| 2013/0267791 A1 * | 10/2013 | Halperin et al. | 600/300 |

\* cited by examiner

*Primary Examiner* — Michael Kahelin
*Assistant Examiner* — Tho Tran
(74) *Attorney, Agent, or Firm* — Scot A. Reader

(57) ABSTRACT

An acoustic physiological monitoring system and method wherein the usability for physiological monitoring of time segments of an acoustic signal recording body sounds is determined using frequency analysis. A time segment of the acoustic signal is filtered into a target portion in a target frequency band and a non-target portion in a non-target frequency band. Energies of the target portion and the non-target portion are computed. A usability indicator for the time segment is computed using the energies. The usability of the time segment is determined using the usability indicator. A physiological parameter estimate is selectively calculated using the time segment based on the usability of the time segment. Finally, information based on the physiological parameter estimate is outputted.

10 Claims, 2 Drawing Sheets

DETERMINING USABILITY OF AN ACOUSTIC SIGNAL FOR PHYSIOLOGICAL MONITORING USING FREQUENCY ANALYSIS

BACKGROUND OF THE INVENTION

The present invention relates to physiological monitoring and, more particularly, noise handling in acoustic physiological monitoring.

Real-time physiological monitoring can be helpful in maintaining the health of people as they go about their daily lives. For example, real-time physiological monitoring can enable prompt discovery of a problem with the respiration of a person who suffers from a chronic pulmonary disease or works in a hazardous environment so that the person can obtain emergency medical treatment. Real-time physiological monitoring can be also used to rapidly detect other types of physiological ailments, such as heart maladies, and can be applied in other contexts, such as senior monitoring and sleep monitoring.

Real-time physiological monitoring often invokes the body sound method, which is sometimes called auscultation. In the body sound method, an acoustic transducer mounted on the body of the person captures and acquires an acoustic signal recording respiration and heart sounds. The sound transducer is typically placed over the suprasternal notch or at the lateral neck near the pharynx because the sounds captured in that region typically have a high signal-to-noise ratio and high sensitivity to variation in flow. Once the acoustic signal has been generated, a respiration sequence may be identified in the acoustic signal and respiration parameter estimates (e.g., respiration rate, inspiration/expiration ratio, etc.) may be calculated. Heart rate estimates may also be calculated from a pulse sequence. Health status information based on respiration parameter estimates and heart rate estimates may then be outputted locally to the monitored person or remotely to a clinician.

One problem commonly encountered in real-time acoustic physiological monitoring is parameter estimation error caused by noise. An acoustic signal that records body sounds can be disrupted by several types of noise, such as long-term, moderate amplitude noise introduced by the surrounding environment, or short-term, high amplitude noise introduced by impulse events such as talking, coughing or sneezing. Regardless of the source, noise can mask the vital signs of interest, resulting in erroneous estimation of physiological parameters and outputting of erroneous health status information. In turn, reliance on erroneous health status information can have serious adverse consequences on the health of the monitored person. For example, such information can lead the person or his or her clinician to improperly diagnose health status and cause the person to undergo treatment that is not medically indicated or forego treatment that is medically indicated.

One known approach to combating noise-induced physiological parameter estimation error tries to remove the noise from the acoustic signal, such as by using a reference microphone to measure environmental noise and attempting to cancel the noise through differentiation. However, this approach adds substantial complexity to the monitoring system and at best only offers a piecemeal solution.

Another known approach, disclosed in Fu et al. application Ser. No. 13/065,816, subjects the acoustic signal to dual path analysis, one path configured to detect long-term moderate amplitude noise and another path configured to detect short-term, high amplitude noise, designates portions of the acoustic signal as noisy based on the combined results of the dual path analysis and excludes the noisy portions when estimating physiological parameters. However, this approach adds meaningfully to the complexity of the monitoring system and tends to be more effective at detecting short-term, high amplitude noise than other types of noise.

SUMMARY OF THE INVENTION

The present invention provides an acoustic physiological monitoring system and method wherein the usability for physiological monitoring of time segments of an acoustic signal is determined using frequency analysis.

In one aspect of the invention, an acoustic physiological monitoring method comprises the steps of receiving by a physiological monitoring system a time segment of an acoustic signal recording body sounds; filtering by the system the time segment into a target portion in a target frequency band and at least one non-target portion in at least one non-target frequency band; computing by the system an energy of the target portion; computing by the system an energy of the non-target portion; computing by the system at least one usability indicator for the time segment based at least in part on the energy of the target portion and the energy of the non-target portion; determining by the system a usability of the time segment based at least in part on the usability indicator; selectively calculating by the system a physiological parameter estimate using the time segment based at least in part on the usability of the time segment; and outputting by the system information based at least in part on the physiological parameter estimate.

In some embodiments, the target portion isolates respiration sounds.

In some embodiments, the target frequency band and the non-target frequency band are adjacent in the frequency domain.

In some embodiments, the target frequency band and the non-target frequency band are non-overlapping in the frequency domain.

In some embodiments, the usability indicator is determined using a ratio of the energy of the target portion to the energy of the non-target portion.

In some embodiments, the usability indicator is determined using a sum of the energy of the target portion and the non-target portion.

In some embodiments, the filtering step is performed using a plurality of bandpass filters.

In some embodiments, the step of determining usability comprises classifying the time segment as one of usable or non-usable.

In some embodiments, the method further comprises the step of reclassifying the time segment as one of usable or non-usable based at least in part on classifications of one or more neighboring time segments as usable or non-usable.

In some embodiments, the step of determining usability comprises assigning to the time segment a probability greater than zero and less than one that the time segment is usable.

In some embodiments, the method further comprises the step of adjusting the probability that the time segment is usable based at least in part on probabilities that one or more neighboring time segments are usable.

In some embodiments, the physiological parameter estimate is a respiration parameter estimate.

In some embodiments, the step of computing at least one usability indicator for the time segment comprises computing a plurality of usability indicators for the time segment.

In another aspect of the invention, a physiological monitoring device comprises a sound capture system configured to generate an acoustic signal recording body sounds; an acoustic signal processing system configured to receive from the sound capture system the signal, filter a time segment of the signal into a target portion in a target frequency band and at least one non-target portion in at least one non-target frequency band, compute an energy of the target portion, compute an energy of the non-target portion, compute at least one usability indicator for the time segment based at least in part on the energy of the target portion and the energy of the non-target portion, determine a usability of the time segment based at least in part on the usability indicator and selectively calculate a physiological parameter estimate using the time segment based at least in part on the usability of the time segment; and a physiological data output system configured to output information based at least in part on the physiological parameter estimate.

These and other aspects of the invention will be better understood by reference to the following detailed description taken in conjunction with the drawings that are briefly described below. Of course, the invention is defined by the appended claims.

DETAILED DESCRIPTION OF A PREFERRED EMBODIMENT

Figure 1:
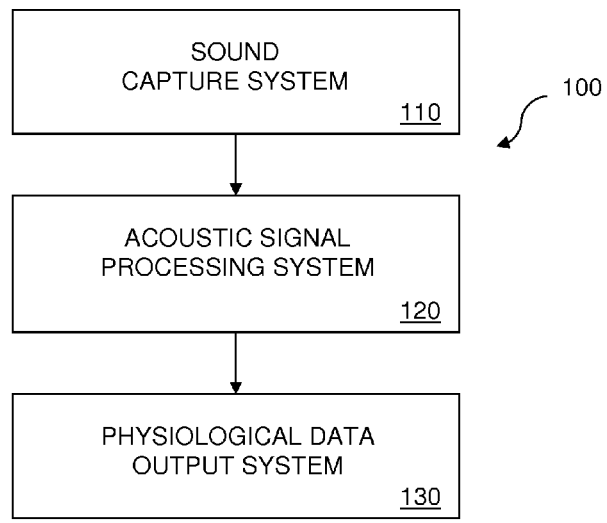
FIG. 1 shows an acoustic physiological monitoring device in some embodiments of the invention.

FIG. 1 shows an acoustic physiological monitoring device 100 in some embodiments of the invention. Monitoring device 100 includes a sound capture system 110, an acoustic signal processing system 120 and a physiological data output system 130, which are communicatively coupled in series.

Capture system 110 continually detects body sounds, such as lung and heart sounds, at a detection point, such as the trachea, chest or back of a person being monitored, and continually transmits an acoustic signal recording the detected body sounds to processing system 120. Capture system 110 may include, for example, a sound transducer positioned on the body of a human subjects that detects body sounds, as well as amplifiers, filters an analog/digital converter and/or automatic gain control that generate an acoustic signal embodying the detected body sounds.

Processing system 120, under control of a processor executing software instructions, continually processes the acoustic signal and generates estimates of one or more physiological parameters for the subject being monitored using usable time segments of the acoustic signal. In some embodiments, monitored physiological parameters include one or more respiration parameters, such as respiration rate, fractional inspiration time and/or inspiration to expiration time ratio. In some embodiments, monitored physiological parameters additionally or alternatively include one or more non-respiration parameters, such as heart rate.

To enable reliable estimation of physiological parameters, processing system 120 continually evaluates the usability for physiological monitoring of individual time segments of the acoustic signal and either includes or excludes the individual time segments from the calculation of physiological parameter estimates based on their usability. The usability of individual time segments is determined based on whether or the extent to which the time segment is "clear", meaning that the body sound of interest (e.g., respiration sound) is recoverable from the time segment, or "mixed", meaning that the body sound of interest is contaminated by noise or other interference in the time segment so as to be unrecoverable.

In some embodiments, processing system 120 performs at least some of the processing operations described herein in custom logic rather than software.

Output system 130 has a display screen for displaying physiological information determined using physiological parameter estimates received from processing system 120. In some embodiments, output system 130, in addition to a display screen, has an interface to an internal or external data management system that stores physiological information determined using physiological parameter estimates received from processing system 120 and/or an interface that transmits such information to a remote monitoring device, such as a monitoring device at a clinician facility. Physiological information outputted by output system 130 may include physiological parameter estimates received from processing system 120 and/or information derived from physiological parameter estimates, such as a numerical score or color-coded indicator of present health status.

In some embodiments, capture system 110, processing system 120 and output system 130 are part of a portable ambulatory monitoring device that monitors a person's physiological well being in real-time as the person performs daily activities. In other embodiments, capture system 110, processing system 120 and output system 130 may be part of separate devices that are remotely coupled via wired or wireless communication links.

Figure 2:
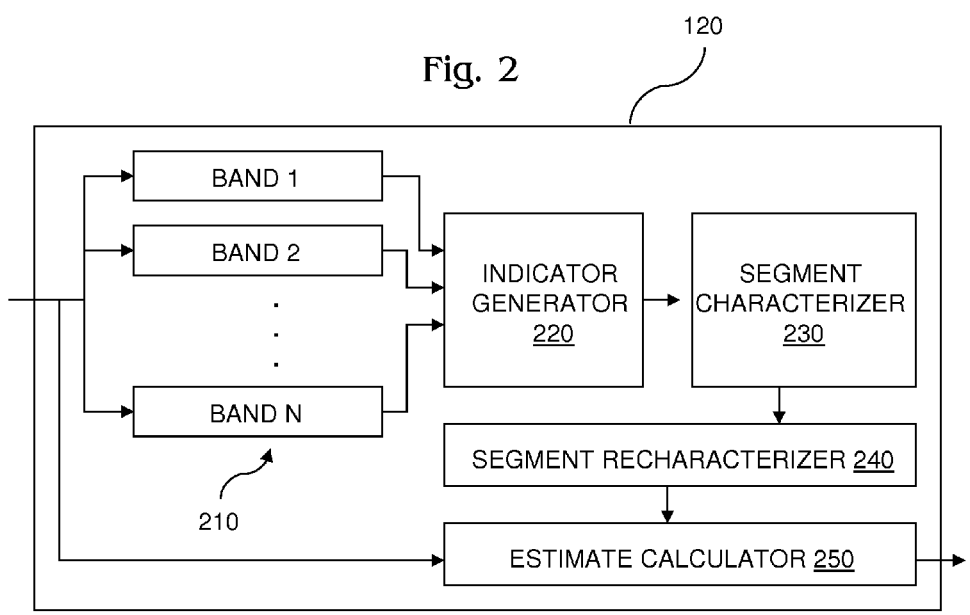
FIG. 2 shows an acoustic signal processing system in some embodiments of the invention.

FIG. 2 shows processing system 120 to include a multiple of band specific energy calculators 210. Energy calculators 210 each include a bandpass filter having a specific passband and an energy computer. The passbands for different ones of energy calculators 210 are configured to be adjacent to each other in the frequency domain with little or no frequency overlap and the passbands for all energy calculators 210 taken together are configured to cover the entire frequency band of the acoustic signal received from capture system 110. Moreover, the passband for one of energy calculators 210 is configured to correspond with a target body sound. For example, since human respiration sounds are typically concentrated between 100 and 600 Hz, if the physiological information outputted by output system 130 includes respiration information, the passband for one of energy calculators 210 is configured to be 100 to 600 Hz. Energy calculators 210 receive an acoustic signal recording body sounds from capture system 110 and, for each time segment of the acoustic signal, compute band specific energy computations for the time segment and deliver them to indicator generator 220. Thus, energy calculators 210 filter each time segment of the acoustic signal into a target portion in a target frequency band and at least one non-target portion in at least one non-target frequency band, separately compute an energy of the target portion and an energy of the non-target portion or portions and deliver the computed energies to an indicator generator 220 for further processing.

The time segments of the acoustic signal treated by processing system 120 are slices of the acoustic signal each spanning a time window of fixed length. In some embodiments, consecutive time segments are non-overlapping. In other embodiments, the time window is a sliding window such that consecutive time segments partially overlap. For example, the fixed length of the time window may be one second and consecutive time windows may be offset from each other by 0.2 seconds.

The energies of the target and non-target portions of the acoustic signal may be computed using various methods. In some embodiments, the energies are computed by summing or averaging absolute values of the acoustic signal amplitude over the time segment. In other embodiments, the energies are computed by summing or averaging squares of the acoustic signal amplitude over the time segment. In still other embodiments, the energies may be computed using standard deviations or variances in acoustic signal amplitude. In still other embodiments, the energies may be computed using peak acoustic signal amplitudes. Depending on the method used for energy computation, the acoustic signal may or may not be downsampled.

Indicator generator 220 generates one or more indicators of usability of time segments of the acoustic signal using the band specific energies computed for the time segments and received from energy calculators 210. These usability indicators are applied by a segment classifier 230 to evaluate the usability of the time segments for computing physiological parameter estimates. To generate usability indicators for a time segment, indicator generator 220 applies the band specific energies computed for the time segment in one or more computations. For example, if the energy of the target portion of the acoustic signal during the time segment is significantly higher than the energies of non-target portions of the acoustic signal during the time segment, that is an indicator that the time segment is clear rather than mixed (e.g., body sound has a high signal to noise ratio) and is usable in computing physiological parameter estimates. As another example, if the total energy of all portions of the acoustic signal during the time segment is significantly above a normal range, that is an indicator that the time segment is mixed rather than clear (e.g., body sound is contaminated by impulse noise) and is not usable for computing physiological parameter estimates. Of course, additional or different computations may be invoked for generating usability indicators. Indicator generator 220 outputs one or more usability indicators for each time segment of the acoustic signal to a segment characterizer 230 for further processing.

Segment characterizer 230 determines the usability of time segments of the acoustic signal using the usability indicators received from indicator generator 220. Segment characterizer 230 determines the usability of each time segment based on whether or the extent to which the usability indicators for the time segment and/or neighboring time segments suggest that the time segment is clear, meaning that the body sound of interest is recoverable from the time segment, or mixed, meaning that the body sound of interest is contaminated by noise or other interference in the time segment so as to be unrecoverable from the time segment. In some embodiments, segment characterizer 230 makes a binary usability determination and each time segment is unambiguously classified as either usable or unusable. In other embodiments, segment characterizer 230 makes a "fuzzy" usability determination and each time segment is assigned a numerical probability between zero and one that the time segment is usable or unusable. In some embodiments, segment characterizer 230 invokes a scoring system in which a score is computed for each time segment using the usability indicators for the time segment and the usability of the time segment is determined based on the score. Moreover, in some of these embodiments, different usability indicators are assigned different weights by the scoring system. Segment characterizer 230 outputs a binary or fuzzy usability assessment for each time segment to segment recharacterizer 240 for further processing.

Segment recharacterizer 240 determines whether to modify the binary or fuzzy usability assessments for time segments of the acoustic signal made by segment characterizer 230 based on one or more predetermined checks. The predetermined checks invoke binary or fuzzy usability assessments from neighboring time segments or other known characteristics of the acoustic signal. For example, even in the absence of substantial noise or interference, where a breathing gap between inspiration and expiration spans a time segment, the energy of the target portion of the acoustic signal during the time segment may not be much higher than the energies of non-target portions of the acoustic signal and the signal may be misclassified by segment characterizer 230 as mixed. In that event, segment recharacterizer 240 can employ a recharacterization check to identify the breathing gap and reclassify the time segment as clear by reference to the binary usability assessments of neighboring time segments. Similarly, where segment characterizer 230 makes fuzzy usability assessments and a time segment has been assigned a numerical probability of being usable by segment characterizer 230, segment recharacterizer 240 may adjust upward or downward the numerical probability based on a check that considers the numerical probabilities assigned to neighboring time segments or other known characteristics of the acoustic signal. Segment recharacterizer 240 outputs a binary usability assessment (e.g., clear or mixed) for each time segment of the acoustic signal to estimate calculator 250 for further processing. Of course, where fuzzy usability assessments are made by segment characterizer 230 (and possibly adjusted by segment recharacterizer 240), segment recharacterizer 240 converts the fuzzy usability assessments to binary usability assessments prior to outputting. For example, where the numerical probability that a time segment is usable is 50 percent or higher, segment recharacterizer 240 may characterize the time segment as clear; and otherwise characterize the time segment is mixed.

Estimate calculator 250 receives the acoustic signal from capture system 110 and the binary usability assessments for time segments of the acoustic signal from segment recharacterizer 240. Estimate calculator 250 continually computes one or more physiological parameter estimates using time segments of the acoustic signal that have been characterized as clear, and excluding time segments of the acoustic signal that have been characterized as mixed. The estimates may include one or more respiration parameter estimates, such as respiration rate, fractional inspiration time and/or inspiration to expiration time ratio estimates. The estimates may additionally or alternatively include one or more non-respiration parameter estimates, such as heart rate estimates. Estimate calculator 250 transmits the estimates to output system 130, which outputs physiological information that may include the estimates themselves and/or information derived from the estimates.

Figure 3:
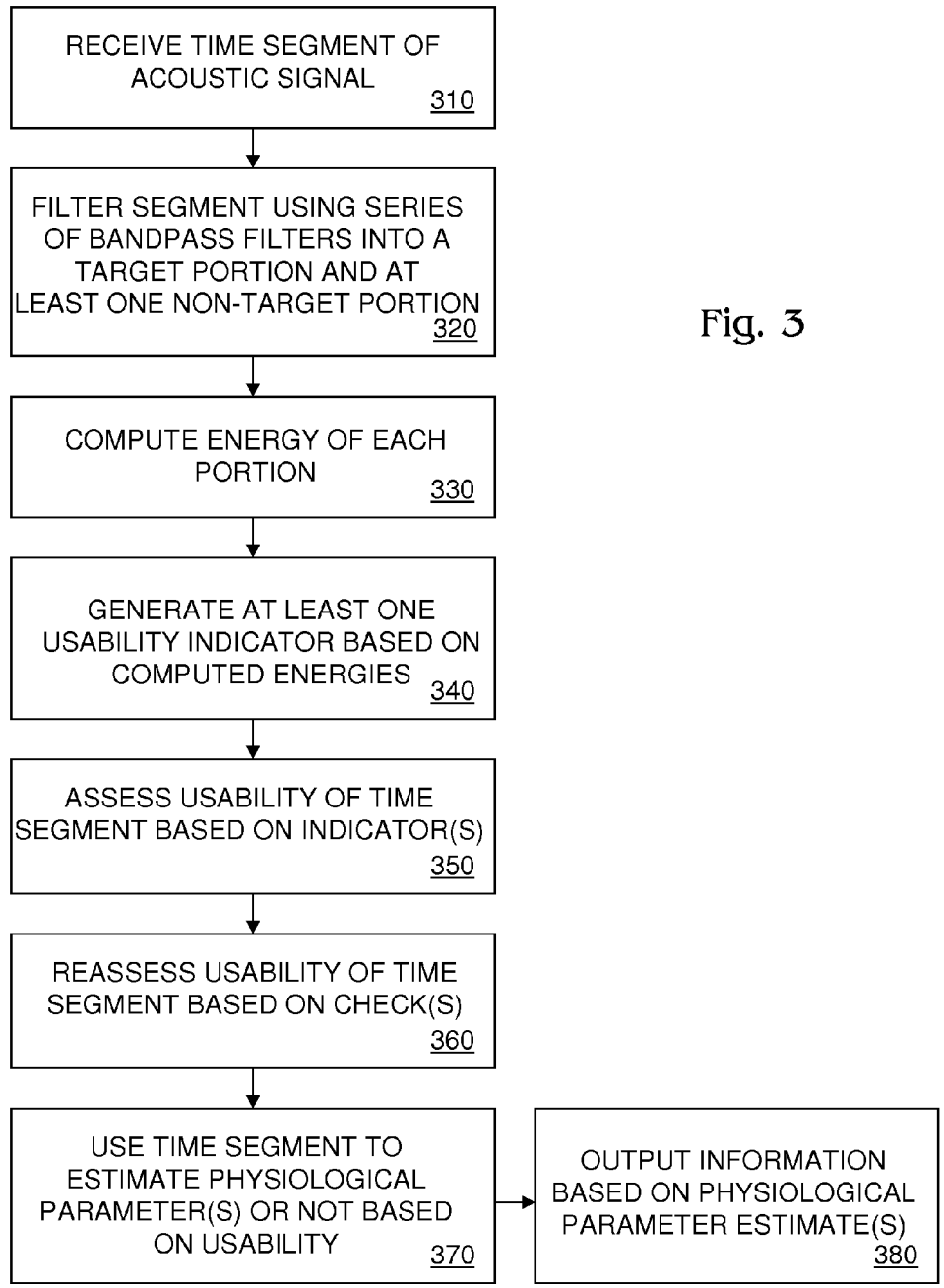
FIG. 3 shows an acoustic physiological monitoring method in some embodiments of the invention.

FIG. 3 shows an acoustic physiological monitoring method in some embodiments of the invention. A time segment of an acoustic signal is received by a physiological monitoring system (310). The system filters the time segment using a series of bandpass filters into a target portion in a target frequency band and at least one non-target portion in at least one non-target frequency band (320). The system computes the energy of each portion of the time segment (330) and generates at least one usability indicator for the time segment using the computed energies (340). The system assesses the usability of the time segment based on the at least one usability indicator (350) and reassesses the usability of the time segment based on at least one predetermined check (360). The system either uses the time segment to estimate one or more physiological parameters or excludes the time segment when estimating such physiological parameters based on the usability of the time segment (370). Finally, the system outputs information based on the physiological parameter estimates (380).

It will be appreciated by those of ordinary skill in the art that the invention can be embodied in other specific forms without departing from the spirit or essential character hereof. The present description is considered in all respects to be illustrative and not restrictive. The scope of the invention is indicated by the appended claims, and all changes that come with in the meaning and range of equivalents thereof are intended to be embraced therein.

What is claimed is:

1. An acoustic physiological monitoring method, comprising the steps of:
   detecting by a physiological monitoring system, using a sound transducer, body sounds;
   generating by the system an acoustic signal expressing the body sounds;
   filtering by the system a time segment of the signal into a target portion in a target frequency band and at least one non-target portion in at least one non-target frequency band;
   computing by the system an energy of the target portion;
   computing by the system an energy of the non-target portion;
   computing by the system a plurality of usability indicators for the time segment by applying a plurality of different rules based at least in part on the energy of the target portion and the energy of the non-target portion, each of the usability indicators providing a separate indication of whether the time segment is clear or mixed;
   determining by the system a usability of the time segment including assigning to the time segment a probability greater than zero and less than one that the time segment is usable based at least in part on the usability indicators and one or more probabilities that one or more neighboring time segments is usable;
   selectively calculating by the system a physiological parameter estimate using the time segment based at least in part on the usability of the time segment; and
   outputting by the system information based at least in part on the physiological parameter estimate.

2. The method of claim 1, wherein the target portion isolates respiration sounds.

3. The method of claim 1, wherein the target frequency band and the non-target frequency band are adjacent in the frequency domain.

4. The method of claim 1, wherein the target frequency band and the non-target frequency band are non-overlapping in the frequency domain.

5. The method of claim 1, wherein at least one of the usability indicator is determined using a ratio of the energy of the target portion to the energy of the non-target portion.

6. The method of claim 1, wherein the filtering step is performed using a plurality of bandpass filters.

7. The method of claim 1, wherein the physiological parameter estimate is a respiration parameter estimate.

8. A physiological monitoring device, comprising:
   a sound capture system configured to detect, using a sound transducer, body sounds and generate an acoustic signal expressing body sounds;
   an acoustic signal processing system configured to receive from the sound capture system the signal, filter a time segment of the signal into a target portion in a target frequency band and at least one non-target portion in at least one non-target frequency band, compute an energy of the target portion, compute an energy of the non-target portion, compute at least one usability indicators for the time segment by applying a plurality of different rules based at least in part on the energy of the target portion and the energy of the non-target portion, each of the usability indicators providing a separate indication of whether the time segment is clear or mixed, determine a usability of the time segment including assigning to the time segment a probability greater than zero and less than one that the time segment is usable based at least in part on the usability indicators and one or more probabilities that one or more neighboring time segments is usable and selectively calculate a physiological parameter estimate using the time segment based at least in part on the usability of the time segment; and
   a physiological data output system configured to output information based at least in part on the physiological parameter estimate.

9. The device of claim 8, wherein at least one of the usability indicators is determined using a ratio of the energy of the target portion to the energy of the non-target portion.

10. The device of claim 8, wherein the device is portable.

* * * * *

UNITED STATES PATENT AND TRADEMARK OFFICE
CERTIFICATE OF CORRECTION

PATENT NO. : 9,241,672 B2  
APPLICATION NO. : 13/369463  
DATED : January 26, 2016  
INVENTOR(S) : Yungkai Kyle Lai Page 1 of 1

It is certified that error appears in the above-identified patent and that said Letters Patent is hereby corrected as shown below:

In the claims

Column 8, line 9, replace "indicator" with --indicators--.

Column 8, line 26, replace "at least one" with --a plurality of--.

Signed and Sealed this  
Nineteenth Day of April, 2016

Michelle K. Lee  
*Director of the United States Patent and Trademark Office*